United States Patent
Choy et al.

(10) Patent No.: US 10,239,817 B2
(45) Date of Patent: Mar. 26, 2019

(54) PROCESS FOR THE PREPARATION OF (1R,3R)- AND (1S,3S)-2,2-DIHALO-3-(SUBSTITUTED PHENYL)CYCLOPROPANECARBOXYLIC ACIDS

(71) Applicant: Dow AgroSciences LLC, Indianapolis, IN (US)

(72) Inventors: Nakyen Choy, Carmel, IN (US); Fangzheng Li, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/727,651

(22) Filed: Oct. 9, 2017

(65) Prior Publication Data

US 2018/0099919 A1    Apr. 12, 2018

Related U.S. Application Data

(60) Provisional application No. 62/406,972, filed on Oct. 12, 2016.

(51) Int. Cl.
    *C07C 51/50* (2006.01)
    *C07C 61/40* (2006.01)
    *C07C 51/487* (2006.01)

(52) U.S. Cl.
    CPC ............ *C07C 51/50* (2013.01); *C07C 51/487* (2013.01); *C07C 61/40* (2013.01); *C07B 2200/07* (2013.01); *C07C 2601/02* (2017.05)

(58) Field of Classification Search
    CPC ....... C07C 51/487; C07C 51/50; C07C 61/40; C07C 2601/02; C07B 2200/07
    See application file for complete search history.

(56) References Cited

U.S. PATENT DOCUMENTS

| | | | |
|---|---|---|---|
| 7,754,717 B2 | 7/2010 | Dimauro et al. |
| 8,067,599 B2 | 11/2011 | Honold et al. |
| 8,492,404 B2 | 7/2013 | Martin et al. |
| 9,781,935 B2 | 10/2017 | Heemstra et al. |
| 9,795,139 B2 | 10/2017 | Eckelbarger et al. |
| 9,795,140 B2 | 10/2017 | Martin et al. |
| 2002/0068838 A1 | 6/2002 | Demassey et al. |
| 2014/0171308 A1 | 6/2014 | Lo et al. |
| 2017/0339961 A1 | 11/2017 | Heemstra et al. |
| 2018/0000087 A1 | 1/2018 | Eckelbarger et al. |
| 2018/0007911 A1 | 1/2018 | Martin et al. |
| 2018/0098541 A1 | 4/2018 | Heemstra et al. |
| 2018/0099919 A1 | 4/2018 | Choy et al. |

FOREIGN PATENT DOCUMENTS

| | | | |
|---|---|---|---|
| WO | 9008126 A1 | 6/1990 |
| WO | 2016168056 A1 | 10/2016 |
| WO | 2016168058 A1 | 10/2016 |
| WO | 2016168059 A1 | 10/2016 |
| WO | 2018071320 A1 | 4/2018 |
| WO | 2018071327 A1 | 4/2018 |

OTHER PUBLICATIONS

Yasukochi et al., "Practical, general, and systematic method for optical resolution of gem-dihalo- and monohalocyclopropanecarboxylic acids utilizing chiral 1,1'-binaphtholmonomethyl ethers: Application to the synthesis of three chiral pesticides," Org. Biomol. Chem., 2008, 6, 540-547. (Year: 2008).*
International Search Report for PCTUS2016026409 aka WO2016168056.
International Search Report for PCTUS2016026413 aka WO2016168058.
International Search Report for PCTUS2016026417 aka WO2016168059.
International Search Report for PCTUS2017055655 aka WO2018071320.
International Search Report for PCTUS2017055738 aka WO2018071327.
Sheshenev A E et al: "Generation and steroselective transformations of 3-phenylcyclopropene", Tetrahedron, Elsevier Science Publishers, Amsterdam, NL, vol. 65, No. 48, Sep. 30, 2009, pp. 100036-100046.
Sheshenev A E et al: "Stereo-and regiocontrol in ene-dimerisation and trimerisation of 1-trimethylsilyl-3-phenylcyclopropene", Tetrahedron, Elsevier Science Publishers, Amsterdam, NL, vol. 65, No. 51, Dec. 19, 2009, pp. 10552-10564.
Written Opinion of the International Search Authority for PCTUS2016026409 aka WO2016168056.
Written Opinion of the International Search Authority for PCTUS2016026413 aka WO2016168058.
Written Opinion of the International Search Authority for PCTUS2016026417 aka WO2016168059.
Written Opinion of the International Search Authority for PCTUS2017055655 aka WO2018071320.
Written Opinion of the International Search Authority for PCTUS2017055738 aka WO2018071327.
V. N. Kovalenko, et al.: "The resolution of trans-2,2-dichloro-3-methylcyclopropanecarboxylic acid via crystallization of its salts with (+)—and (−)-α-phenylethylamine, and the transformation of the resulting enantiomers into (R)—and (S)-dimethyl 2-methylsuccinates", Tetrahedron: Asymmetry, vol. 22, No. 1, Jan. 17, 2011, pp. 26-30, Elsevier Science Publishers, Amsterdam, NL.

* cited by examiner

*Primary Examiner* — Pancham Bakshi
*Assistant Examiner* — Mark R Luderer

(57) ABSTRACT

The (1R,3R)- or (1S,3S)-enantiomer of 2,2-dichloro-3-(substituted phenyl)cyclopropane-carboxylic acid is prepared in a process involving chemical resolution of a racemic mixture of a trans-2,2-dichloro-3-(substituted phenyl)cyclopropanecarboxylic acid with an enantiomeric amine, isolation of a diastereomeric amine salt and finally treatment of the salt with an acid.

10 Claims, No Drawings

PROCESS FOR THE PREPARATION OF (1R,3R)- AND (1S,3S)-2,2-DIHALO-3-(SUBSTITUTED PHENYL)CYCLOPROPANECARBOXYLIC ACIDS

CROSS REFERENCE TO RELATED APPLICATIONS

This application claims the benefit of U.S. Provisional Patent Application Ser. No. 62/406,972, filed Oct. 12, 2016.

TECHNICAL FIELD OF THE DISCLOSURE

This application relates to a process for the preparation of (1R,3R)- and (1S,3S)-2,2-dihalo-3-(substituted phenyl)cyclopropanecarboxylic acids. More particularly, this application relates to a process for chemically resolving racemic trans-2,2-dichloro-3-(substituted phenyl)cyclopropanecarboxylic acids into the (1R,3R)- and (1S,3S)-enantiomers. The process involves treating the racemic acids with a chiral amine to form a crystalline diastereomeric amine salt, and then treating the diastereomeric amine salt with an acid to generate the resolved (1R,3R)- or the (1S,3S)-2,2-dihalo-3-(substituted phenyl)cyclopropanecarboxylic acid.

Definitions of the Disclosure

The following definitions apply to the terms as used throughout this specification, unless otherwise limited in specific instances.

As used herein, the term "phenyl" refers to a aromatic carbocyclic group of 6 carbon atoms which is also referred to herein as Ph. Preferred substituents on the phenyl include F, Cl, Br, I, CN, $NO_2$, $SF_5$, and $C_1$-$C_3$-haloalkyl.

As used herein, the term "benzyl" refers to a $PhCH_2$— group with no substituents on the phenyl group.

As used herein, the term "alkyl" denotes branched or unbranched hydrocarbon chains.

The term "halogen" or "halo" as used herein alone or as part of another group refers to chlorine (Cl), bromine (Br), fluorine (F), and iodine (I).

The term "enantiomeric excess (ee)" as used herein is a measurement of purity used for chiral substances. It reflects the degree to which a sample contains one enantiomer in greater amounts than the other. A racemic mixture has an ee of 0%, while a single, completely pure enantiomer has an ee of 100%.

The terms "resolving" and "resolution" as used herein refer to a chemical process or method whereby a racemic mixture of stereoisomers is separated into the individual enantiomers.

DETAILED DESCRIPTION OF THE DISCLOSURE

The process of the present application is described in detail below.

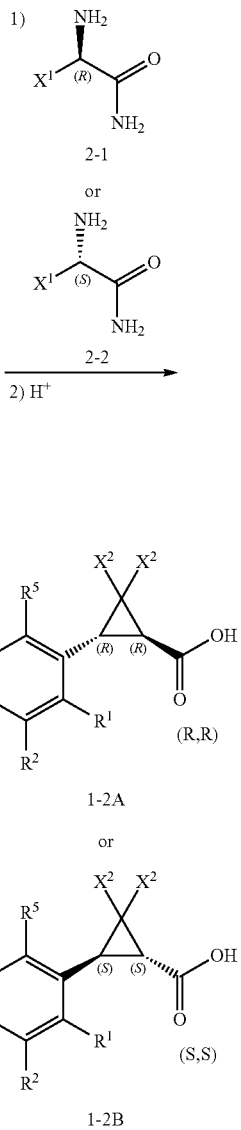

Scheme 1 wherein:
(A) $R^1$ is selected from the group consisting of H, F, Cl, Br, I, CN, $NO_2$, $SF_5$, ($C_1$-$C_3$)alkyl, and ($C_1$-$C_3$)haloalkyl;
(B) $R^2$ is selected from the group consisting of H, F, Cl, Br, I, CN, $NO_2$, $SF_5$, ($C_1$-$C_3$)alkyl, and ($C_1$-$C_3$)haloalkyl;
(C) $R^3$ is selected from the group consisting of H, F, Cl, Br, I, CN, $NO_2$, $SF_5$, ($C_1$-$C_3$)alkyl, and ($C_1$-$C_3$)haloalkyl;
(D) $R^4$ is selected from the group consisting of H, F, Cl, Br, I, CN, $NO_2$, $SF_5$, ($C_1$-$C_3$)alkyl, and ($C_1$-$C_3$)haloalkyl;
(E) $R^5$ is selected from the group consisting of H, F, Cl, Br, I, CN, $NO_2$, $SF_5$, ($C_1$-$C_3$)alkyl, and ($C_1$-$C_3$)haloalkyl;
(F) $X^1$ is selected from the group consisting of $C_1$-$C_4$ alkyl or benzyl; and
(G) $X^2$ is selected from the group consisting of F, Cl, Br, and I.

In Scheme 1, the (±)-trans-racemate of Formula 1-1 (i.e., the mixture of (R,R) and (S,S) enantiomers of a trans-2,2-dichloro-3-(substituted phenyl)cyclopropane-carboxylic acid) is combined with a resolving agent that is either the enantiomeric amine of Formula 2-1 or Formula 2-2, in a suitable solvent, to provide the diastereomeric amine salts of Formula 3-1A or Formula 3-1B,

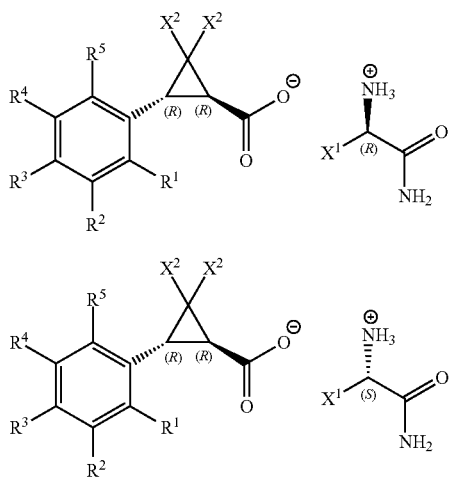

or of Formula 3-2A or Formula 3-2B,

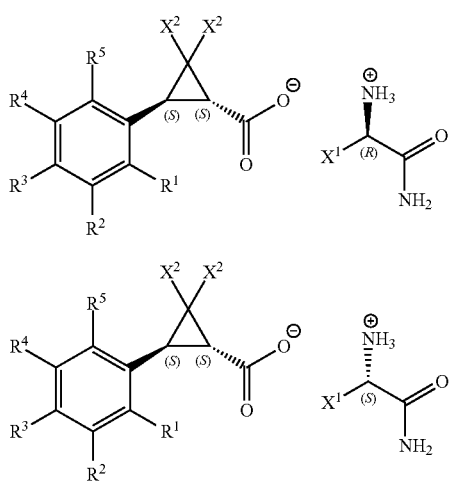

that selectively crystallize or precipitate out of the resulting mixture (Step 1 of the process). The diastereomeric amine salt of Formula 3-1A or Formula 3-1B, or of Formula 3-2A or Formula 3-2B, can then be isolated from the mixture and treated with an acid to provide the (1R,3R)- or the (1S,3S)-2,2-dihalo-3-(substituted phenyl)cyclopropanecarboxylic acid of Formula 1-2A or Formula 1-2B, respectively (Step 2 of the process).

Consequently, in light of the above, the following embodiments (D) are envisioned.

1D. The process for preparing the (1R,3R) enantiomer of the 2,2-dihalo-3-(substituted phenyl)cyclopropanecarboxylic acid of Formula 1-2A from the racemic mixture of Formula 1-1 comprising treating the racemic mixture with a resolving agent that is the (R)-enantiomeric amine of Formula 2-1.

The process for preparing the (1R,3R) enantiomer of the 2,2-dichloro-3-(substituted phenyl)cyclopropanecarboxylic acid of Formula 1-2A from the racemic mixture of Formula 1-1 comprising treating the racemic mixture with a resolving agent that is the (R)-enantiomeric amine of Formula 2-1. The process for preparing the (1R,3R) enantiomer of the 2,2-dihalo-3-(substituted phenyl)cyclopropanecarboxylic acid of Formula 1-2A from the racemic mixture of Formula 1-1 comprising treating the racemic mixture with a resolving agent that is the (R)-enantiomeric amine of Formula 2-1, wherein said halos of the 2,2-dihalo are not the same.

2D. The process for preparing the (1R,3R) enantiomer of the 2,2-dichloro-3-(substituted phenyl)cyclopropanecarboxylic acid of Formula 1-2A from the racemic mixture of Formula 1-1 comprising treating the racemic mixture with a resolving agent that is the (S)-enantiomeric amine of Formula 2-2.

3D. The process for preparing the (1S,3S) enantiomer of the 2,2-dichloro-3-(substituted phenyl)cyclopropanecarboxylic acid of Formula 1-2B from the racemic mixture of Formula 1-1 comprising treating the racemic mixture with a resolving agent that is the (R)-enantiomeric amine of Formula 2-1.

4D. The process for preparing the (1S,3S) enantiomer of the 2,2-dihalo-3-(substituted phenyl)cyclopropanecarboxylic acid of Formula 1-2B from the racemic mixture of Formula 1-1 comprising treating the racemic mixture with a resolving agent that is the (S)-enantiomeric amine of Formula 2-2. The process for preparing the (1S,3S) enantiomer of the 2,2-dichloro-3-(substituted phenyl)cyclopropanecarboxylic acid of Formula 1-2B from the racemic mixture of Formula 1-1 comprising treating the racemic mixture with a resolving agent that is the (S)-enantiomeric amine of Formula 2-2. The process for preparing the (1S,3S) enantiomer of the 2,2-dihalo-3-(substituted phenyl)cyclopropanecarboxylic acid of Formula 1-2B from the racemic mixture of Formula 1-1 comprising treating the racemic mixture with a resolving agent that is the (S)-enantiomeric amine of Formula 2-2 wherein said halos of the 2,2-dihalo are not the same.

5D. The molar equivalents of the resolving agent of Formula 2-1 or Formula 2-2 used in Step 1 of the process relative to the racemic trans-2,2-dichloro-3-(substituted phenyl)cyclopropanecarboxylic acid of Formula 1-1 may range from about 0.4 to about 0.8, preferably from about 0.5 to about 0.7.

6D. Solvents for use in Step 1 of the process may include protic and aprotic solvents such as, but not limited to, acetonitrile ($CH_3CN$), acetone, isopropyl alcohol (IPA), ethanol (EtOH), ethyl acetate (EtOAc), and mixtures thereof. In addition, solvent systems including a polar and a non-polar solvent such as, for example, EtOAc-heptane, IPA-heptane, and the like, may also be used.

7D. The concentration of the (±)-trans-racemate of Formula 1-1 in Step 1 of the process may range from about 0.05 molar to about 1.00 molar, preferably from about 0.25 to about 0.60 molar.

8D. Step 1 of the process may be conducted at temperatures that range from about −20 to about 100° C. or from about 10 to about 80° C., including starting at above room temperature (RT) and then cooling to RT or below RT. The process may be conducted for a period of time of about 1 hour to about 20 hours.

9D. Step 1 of the process is normally conducted at atmospheric pressure, but may be conducted at pressures ranging from about 1 atmosphere to about 10 atmospheres of pressure.

10D. In Step 2 of the process, the acid may be selected from the group including hydrochloric acid (HCl), hydrobromic acid (HBr), sulfuric acid ($H_2SO_4$), phosphoric acid ($H_3PO_4$), and nitric acid ($HNO_3$).

11D. In Step 1 of the process, the resolving agent that is the enantiomeric amine of Formula 2-2 is the compound of Formula 2-2A, (L)-leucinamide:

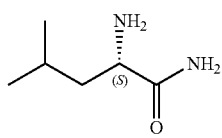

2-2A

12D. In Step 1 of the process, the resolving agent that is the enantiomeric amine of Formula 2-1 is the compound of Formula 2-1A, (D)-phenylalanine amide:

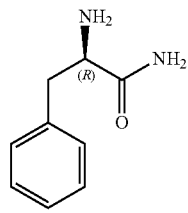

2-1A

13D. In Step 1 of the process, the resolving agent that is the enantiomeric amine of Formula 2-2 is the compound of Formula 2-2A, (L)-phenylalanine amide:

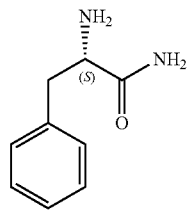

2-2A

14D. A process for the preparation of (1R,3R)-2,2-dichloro-3-(3-trifluoromethyl-4-fluorophenyl)cyclopropanecarboxylic acid of Formula 4-1

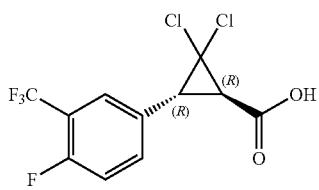

4-1 comprising:
a) treating a racemic mixture of trans-2,2-dichloro-3-(3-trifluoromethyl-4-fluorophenyl)cyclopropane-carboxylic acid of Formula 4-2

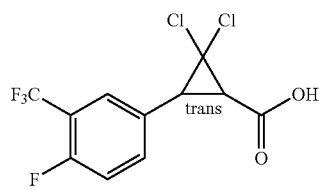

4-2 with an enantiomeric amine of Formula 2-2A

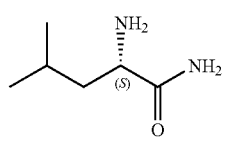

2-2A to form a mixture;
b) isolating a diastereomeric amine salt of Formula 4-3

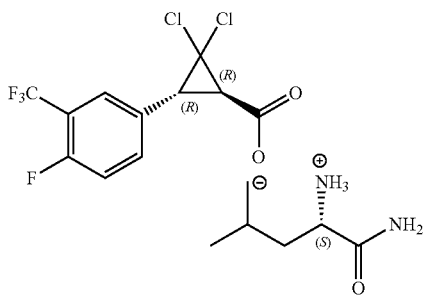

4-3 from the mixture; and
c) treating the isolated diastereomeric amine salt of Formula 4-3 with an acid to provide the (1R,3R)-2,2-dichloro-3-(3-trifluoromethyl-4-fluorophenyl)cyclopropanecarboxylic acid of Formula 4-1.

Embodiments 1D through 14D, may be used in any combination.

EXAMPLES

These examples are for illustration purposes and are not to be construed as limiting this disclosure to only the embodiments disclosed in these examples.

Starting materials, reagents, and solvents that were obtained from commercial sources were used without further purification. Melting points are uncorrected. Examples using "room temperature" were conducted in climate controlled laboratories with temperatures ranging from about 20° C. to about 24° C. Molecules are given their known names, named according to naming programs within Accelrys Draw, ChemDraw, or ACD Name Pro. If such programs are unable to name a molecule, such molecule is named using conventional naming rules. 1H NMR spectral data are in ppm (δ) and were recorded at 300, 400, 500, or 600 MHz; 13C NMR spectral data are in ppm (δ) and were recorded at 75, 100, or 150 MHz, and 19F NMR spectral data are in ppm (δ) and were recorded at 376 MHz, unless otherwise stated.

Enantiomeric excess values (ee %) was determined by Chiral HPLC method as follows: Column: CHIRALPAK©

ZWIX(+), particle size 3 μm, dimension 3 mm×150 mm, DAIC 511584; Mobile phase which is a mixture of 500 mL acetonitrile, 500 mL methanol, 20 mL water, 1.9 mL formic acid, and 2.6 mL diethylamine; Flow rate: 0.5 mL/min; Time: 9 min; Temperature: 25° C.

Isolated yields of the resolved (1R,3R)- and (1S,3S)-2,2-dichloro-3-(substituted phenyl)cyclopropane-1-carboxylic acids are based on the total weight of starting racemic trans-2,2-dihalo-3-(substituted phenyl)cyclopropane-1-carboxylic acid mixture used in the resolution.

Example 1

Resolution of racemic trans-2,2-dichloro-3-(3,5-dichlorophenyl)cyclopropane-1-carboxylic acid with (L)-leucinamide to provide (1R,3R)-2,2-dichloro-3-(3,5-dichlorophenyl)cyclopropane-1-carboxylic acid

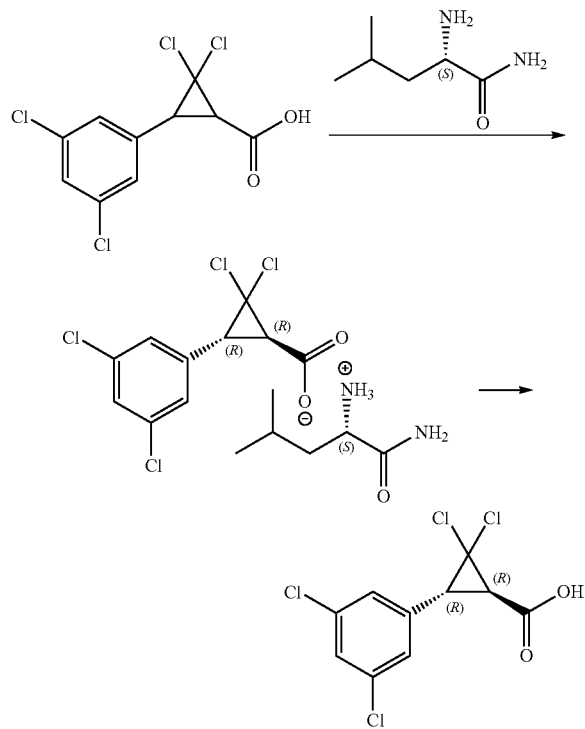

A mixture of (L)-leucinamide (163 mg, 1.25 mmol) and racemic trans-2,2-dichloro-3-(3,5-dichlorophenyl)cyclopropane-carboxylic acid) (750 mg, 2.5 mmol) in acetonitrile (20 mL) was stirred at 60° C. for 0.5 hours. After a solid began to deposit, the mixture placed at room temperature for 4 hours. The white solid was collected, washed with minimal acetonitrile and dried: $^1$H NMR (400 MHz, DMSO-d$^6$) δ 7.81 (s, 1H), 7.53 (t, J=1.9 Hz, 1H), 7.43 (d, J=1.9 Hz, 2H), 7.31 (s, 1H), 3.58-3.44 (m, 1H), 3.27 (d, J=8.6 Hz, 1H), 3.08 (d, J=8.6 Hz, 1H), 1.68 (dt, J=13.3, 6.6 Hz, 1H), 1.49 (dt, J=10.1, 6.8 Hz, 2H), 0.89 (t, J=6.7 Hz, 6H). The white solid salt was diluted with EtOAc and washed with 1N HCl and brine solution. The organic layer was dried over Na$_2$SO$_4$, filtered and concentrated to afford the title product as a white solid: (202 mg, 91% ee, 27% yield); $^1$H NMR (300 MHz, CDCl$_3$) δ 7.36 (t, J=1.9 Hz, 1H), 7.17 (dd, J=1.9, 0.7 Hz, 2H), 3.48-3.37 (m, 1H), 2.87 (d, J=8.3 Hz, 1H). $^{13}$C NMR (400 MHz, DMSO-d$^6$) δ 166.28, 136.40, 133.39, 127.27, 127.04, 61.36, 37.10, 35.98. LCMS m/z=298.9 [M+H].

Example 2

Resolution of racemic trans-2,2-dichloro-3-(3-chloro-4-fluorophenyl)cyclopropane-1-carboxylic acid with (L)-leucinamide to provide (R,R)-trans-2,2-dichloro-3-(3-chloro-4-fluorophenyl)cyclopropane-1-carboxylic acid

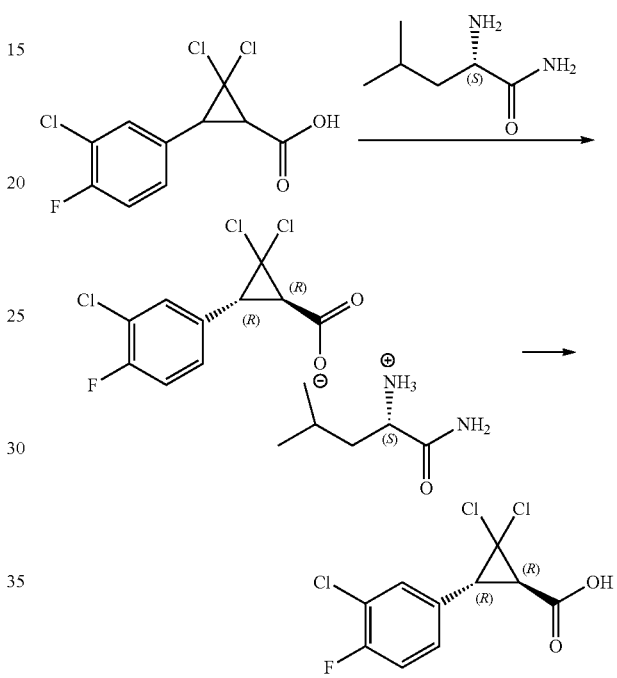

A mixture of (L)-leucinamide (0.45 g, 3.5 mmol) and racemic trans-2,2-dichloro-3-(3-chloro-4-fluorophenyl)cyclopropane-carboxylic acid) (1.41 g, 5 mmol) in acetonitrile (20 mL) was stirred at 60° C. for 0.5 hours. After a solid began to deposit, the mixture was placed at room temperature for 4 hours. The white solid was collected, washed with minimal acetonitrile and dried: 1H NMR (400 MHz, DMSO-d6) δ 7.81 (s, 1H), 7.53 (t, J=1.9 Hz, 1H), 7.43 (d, J=1.9 Hz, 2H), 7.31 (s, 1H), 3.58-3.44 (m, 1H), 3.27 (d, J=8.6 Hz, 1H), 3.08 (d, J=8.6 Hz, 1H), 1.68 (dt, J=13.3, 6.6 Hz, 1H), 1.49 (dt, J=10.1, 6.8 Hz, 2H), 0.89 (t, J=6.7 Hz, 6H).

The white solid salt was diluted with EtOAc and washed with 1N HCl and brine solution. The organic layer was dried over Na$_2$SO$_4$, filtered and concentrated to afford the title product as a white solid: (640 mg, 91% ee, 45% yield); 1H NMR (400 MHz, DMSO-d6) δ 13.29 (s, 1H), 7.72 (dd, J=7.1, 2.1 Hz, 1H), 7.56-7.32 (m, 2H), 3.46 (d, J=1.0 Hz, 2H); 19F NMR (376 MHz, DMSO-d6) δ -117.35.

Example 3

Resolution of racemic trans-2,2-dichloro-3-(3,4-dichlorophenyl)cyclopropane-1-carboxylic acid with (L)-leucinamide to provide (R,R)-trans-2,2-dichloro-3-(3,4-dichlorophenyl)cyclopropane-1-carboxylic acid

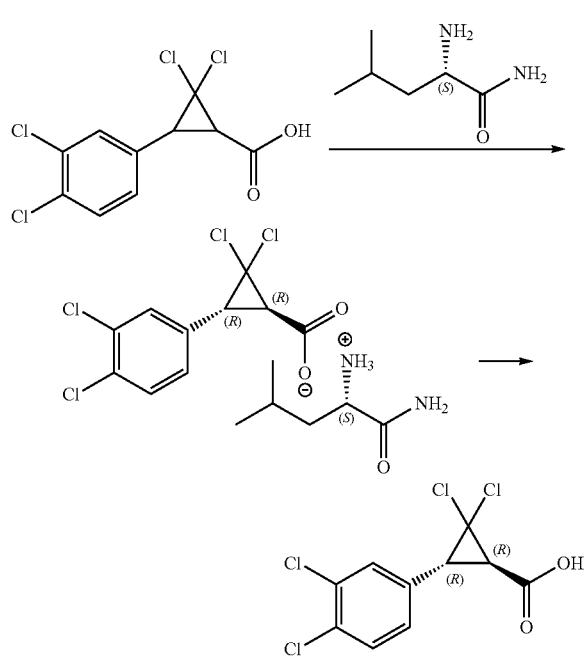

A mixture of (L)-leucinamide (326 mg, 2.5 mmol) and racemic trans-2,2-dichloro-3-(3,4-dichlorophenyl)cyclopropane-carboxylic acid) (1.5 g, 5 mmol) in acetonitrile (20 mL) was stirred at 60° C. for 0.5 hours. After a solid began to deposit, the mixture was placed at room temperature for 4 hours. The solid was collected, washed with minimal acetonitrile and dried: $^1$H NMR (400 MHz, DMSO-d$^6$) δ 7.72 (s, 1H), 7.64 (d, J=2.1 Hz, 1H), 7.60 (d, J=8.3 Hz, 1H), 7.34 (dd, J=8.4, 2.1 Hz, 1H), 7.31-7.26 (m, 1H), 3.48 (dd, J=8.2, 6.2 Hz, 1H), 3.26 (d, J=8.6 Hz, 1H), 3.03 (d, J=8.7 Hz, 1H), 1.74-1.57 (m, 1H), 1.47 (ddd, J=14.6, 7.7, 6.1 Hz, 2H), 0.89 (t, J=6.9 Hz, 6H).

The white solid salt was diluted with EtOAc and washed with 1N HCl and brine solution. The organic layer was dried over Na$_2$SO$_4$, filtered and concentrated to afford the title product as a white solid: (560 mg, 96% ee, 36% yield); $^1$H NMR (500 MHz, DMSO-d$^6$) δ 13.39 (s, 1H), 7.76 (d, J=2.1 Hz, 1H), 7.64 (d, J=8.3 Hz, 1H), 7.44 (dd, J=8.4, 2.1 Hz, 1H), 3.49 (s, 2H). $^{13}$C NMR (126 MHz, DMSO) δ 166.34, 133.35, 130.47, 130.33, 130.09, 129.77, 128.81, 61.43, 37.00, 36.06. LCMS m/z=298.9 [M+H].

Example 4

Resolution of racemic trans-2,2-dichloro-3-(3-trifluoromethyl-4-fluorophenyl)cyclopropane-1-carboxylic acid with (L)-leucinamide to provide (1R,3R)-2,2-dichloro-3-(3-trifluoromethyl-4-fluorophenyl)cyclopropane-1-carboxylic acid

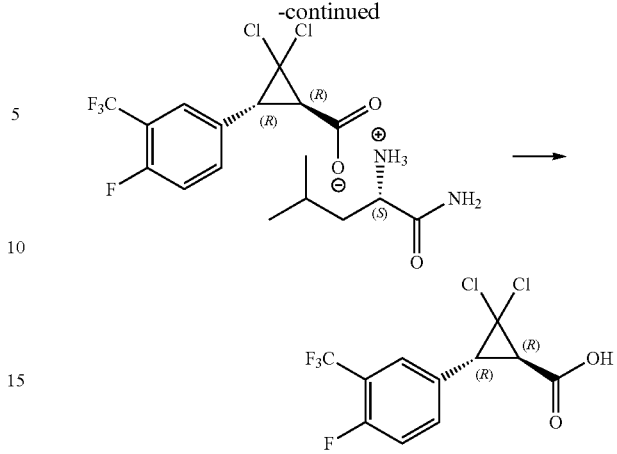

A mixture of (L)-leucinamide (15.6 g, 120 mmol) and racemic trans-2,2-dichloro-3-(3-trifluoromethyl-4-fluorophenyl)cyclopropane-1-carboxylic acid (63.4 g, 200 mmol) in acetonitrile (800 mL) was stirred at 60° C. for 1 hr. After a solid began to deposit, the mixture was placed at room temperature for 4 hours. The solid was collected, washed with minimal acetonitrile and dried to afford the salt of (L)-leucinamide and trans-(1R,3R)-2,2-dichloro-3-(4-fluoro-3-(trifluoromethyl)phenyl)cyclopropane-1-carboxylate as a white solid: (38.9 g, 95% ee, 43%); $^1$H NMR (400 MHz, DMSO-d$^6$) δ 7.80 (s, 1H), 7.73 (m, Hz, 2H), 7.49 (dd, J=10.7, 8.6 Hz, 1H), 7.31 (s, 1H), 3.53 (dd, J=7.9, 6.4 Hz, 1H), 3.34 (d, J=8.6 Hz, 1H), 3.07 (d, J=8.6 Hz, 1H), 1.77-1.60 (m, 1H), 1.60-1.40 (m, 2H), 0.89 (t, J=6.7 Hz, 6H); $^{19}$F NMR (376 MHz, DMSO) δ -59.88, -117.93.

The white solid salt was diluted with EtOAc and washed with 1.5N HCl and water. The organic layer was dried over Na$_2$SO$_4$, filtered and concentrated to afford the title product as a white solid (27.3 g, 95% ee, 43% yield). $^1$H NMR (400 MHz, DMSO-d$^6$) δ 13.24 (s, 1H), 8.03-7.71 (m, 2H), 7.54 (dd, J=10.6, 8.7 Hz, 1H), 3.65-3.51 (m, 2H); $^{19}$F NMR (376 MHz, DMSO-d$^6$) δ -59.93, -117.06; LCMS m/z=316 [M−H].

Example 5

Resolution of racemic trans-2,2-dichloro-3-(4-fluoro-3-(trifluoromethyl)phenyl)cyclopropane-1-carboxylic acid with (R)-2-amino-3-phenylpropanamide ((D)-phenylalanine) to provide (R)-2-amino-3-phenylpropanamide (1R,3R)-2,2-dichloro-3-(4-fluoro-3-(trifluoromethyl)phenyl)cyclopropane-1-carboxylate

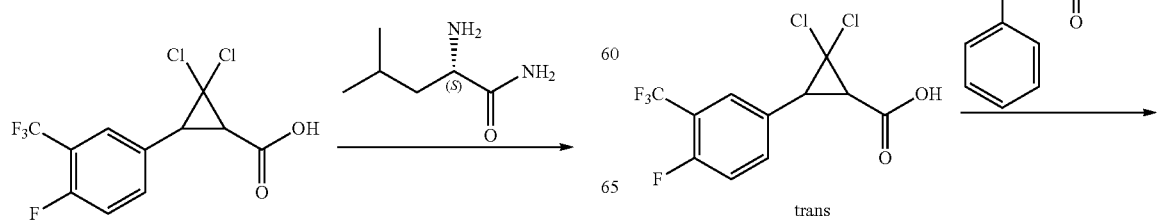

trans

-continued

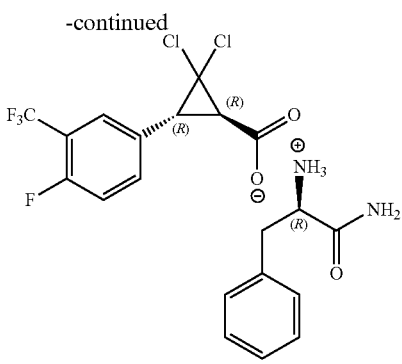

In a flask with a magnetic stirrer, a mixture of 2,2-dichloro-3-(4-fluoro-3-(trifluoromethyl)phenyl)cyclopropane-1-carboxylic acid (1.58 g, 5.0 mmol) and (R)-2-amino-3-phenylpropanamide (411 mg, 2.5 mmol) in acetonitrile (20 mL) was heated to 60° C. The resulting suspension was stirred at 60° C. for 10 min, then cooled to RT. The mixture was stirred overnight. The product was filtered and washed with acetonitrile, then dried in air and at 35° C. in a vacuum oven to give (R)-2-amino-3-phenylpropanamide (1R,3R)-2,2-dichloro-3-(4-fluoro-3-(trifluoromethyl)phenyl)cyclopropane-1-carboxylate (710 mg, 1.475 mmol, 29.5% yield) as a white solid. Chiral HPLC analysis indicated the ratio of SS/RR was 6/93 (86% ee).

Example 6

Resolution of racemic trans-2,2-dichloro-3-(4-fluoro-3-(trifluoromethyl)phenyl)cyclopropane-1-carboxylic acid with (S)-2-amino-3-phenylpropanamide to provide (S)-2-amino-3-phenylpropanamide (1S,3S)-2,2-dichloro-3-(4-fluoro-3-(trifluoromethyl)phenyl)cyclopropane-1-carboxylate

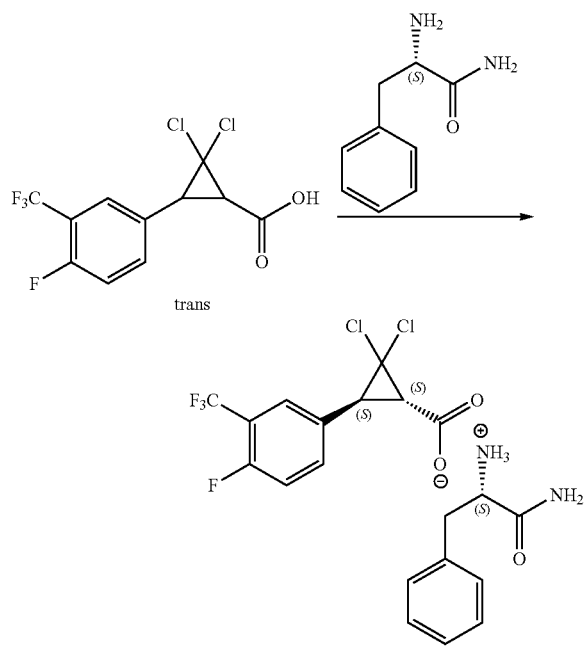

In a flask with a magnetic stirrer, a mixture of racemic 2,2-dichloro-3-(4-fluoro-3-(trifluoromethyl)phenyl)cyclopropane-1-carboxylic acid (1.58 g, 5.0 mmol) and (S)-2-amino-3-phenylpropanamide (411 mg, 2.5 mmol) in acetonitrile (ACN, 20 mL) was heated to 60° C. The resulting suspension was stirred at 60° C. for 10 min, then cooled to rt. The mixture was stirred overnight. The product was filtered and washed with ACN, then dried in air and at 35° C. in a vacuum oven to give (S)-2-amino-3-phenylpropanamide (1S,3S)-2,2-dichloro-3-(4-fluoro-3-(trifluoromethyl)phenyl)cyclopropane-1-carboxylate (669 mg, 1.390 mmol, 27.8% yield) as a white solid. The chiral HPLC indicated the ratio of SS/RR was 96/3 (93 (Nee).

COMPARATIVE EXAMPLES (CE)

Example CE-1

Resolution of racemic trans-2,2-dichloro-3-(3-trifluoromethyl-4-fluorophenyl)cyclopropane-1-carboxylic acid with (S)-1-phenylethan-1-amine to provide (S)-1-phenylethan-1-amine (1R,3R)-2,2-dichloro-3-(4-fluoro-3-(trifluoromethyl)phenyl) cyclopropane-1-carboxylate

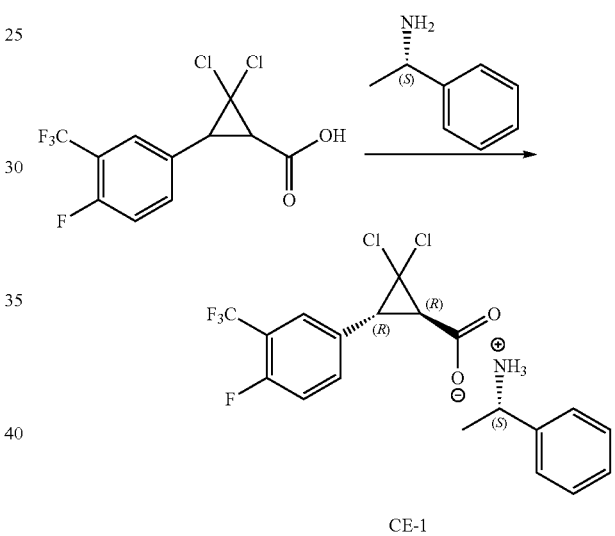

CE-1

Procedure A:

In a flask with magnetic stirrer, a mixture of 2,2-dichloro-3-(4-fluoro-3-(trifluoromethyl)phenyl)cyclopropane-1-carboxylic acid (1.58 g, 5 mmol) and (S)-1-phenylethan-1-amine (303 mg, 2.5 mmol) in acetonitrile (20 mL) was heated at 60° C. The resulting suspension was stirred at 60° C. for 10 min, then cooled to RT. The mixture was stirred overnight. The product was filtered and washed with acetonitrile, then dried in air and then at 35° C. in a vacuum oven to give (S)-1-phenylethan-1-amine (1R,3R)-2,2-dichloro-3-(4-fluoro-3-(trifluoromethyl)phenyl)cyclopropane-1-carboxylate (649 mg, 1.481 mmol, 29.6% yield) as a white solid. Chiral HPLC analysis indicated the ratio of SS/RR enantiomers to be 45/54 (9% ee).

Procedure B:

In a flask with magnetic stirrer, a mixture of racemic 2,2-dichloro-3-(4-fluoro-3-(trifluoromethyl)phenyl)cyclopropane-1-carboxylic acid (0.95 g, 3 mmol) and (S)-1-phenylethan-1-amine (195 mg, 1.5 mmol) in acetone (6 mL) was heated at 50° C. The resulting suspension was stirred at 50° C. for 10 min, then cooled to RT. The mixture was stirred overnight. The product was filtered, washed with acetone, and dried in air and then at 35° C. in a vacuum oven to give (S)-1-phenylethan-1-amine (1R,3R)-2,2-dichloro-3-(4-fluoro-3-(trifluoromethyl)phenyl)cyclopropane-1-carboxylate (228 mg, 0.5 mmol, 16.6% yield) as a white solid. Chiral HPLC analysis indicated the ratio of SS/RR (28/71: 43% ee).

Example CE-1 (Procedures A and B) describes comparative examples showing use of the resolving agent (S)-1-phenylethanamine in acetonitrile and acetone solvents, respectively, to resolve the (1R,3R)-enantiomer from racemic trans-2,2-dichloro-3-(3-trifluoromethyl-4-fluorophenyl)cyclopropane-1-carboxylic acid. This resolving agent has been used as described in Tetrahedron: Asymmetry 2011, 22, pages 26-30, to successfully resolve the (1S,3R) enantiomer from a racemic mixture of a cyclopropanecarboxylic acid compound, racemic trans-2,2-dichloro-3-methylcyclopropanecarboxylic acid, the compound of Formula CE-2. The resolved (1S,3R) enantiomer of CE-2, after 2 recrystallizations, was prepared in 23% yield with a 92% ee.

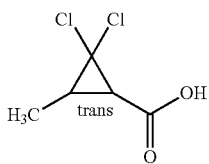

CE-2

When resolving agent (S)-1-phenylethanamine was used to resolve racemic trans-2,2-dichloro-3-(3-trifluoromethyl-4-fluorophenyl)cyclopropane-1-carboxylic acid into the (S)-1-phenylethan-1-amine (1R,3R)-2,2-dichloro-3-(4-fluoro-3-(trifluoromethyl)phenyl)cyclopropane-1-carboxylate as described in Example CE-1 (Procedures A and B), 29.6% and 16.6% yields, respectively, of the (1R,3R)-enantiomer were obtained, providing samples with an ee of only 9% and 43%, respectively.

Using the process of the present application for resolving racemic trans-2,2-dichloro-3-(3-trifluoromethyl-4-fluorophenyl)cyclopropane-1-carboxylic acid with resolving agent (L)-leucinamide (Example 4), (1R,3R)-2,2-dichloro-3-(3-trifluoromethyl-4-fluorophenyl)cyclopropane-1-carboxylic acid was obtained in 43% yield, in very high enantiomeric excess (95% ee), using only one resolution cycle, and with no additional purification.

It should be understood that while this invention has been described herein in terms of specific embodiments set forth in detail, such embodiments are presented by way of illustration of the general principles of the invention, and the invention is not limited thereto. Certain modifications and variations in any given material, process step, or chemical formula, will be readily apparent to those skilled in the art without departing from the true spirit and scope of the present invention, and all such modifications and variations should be considered within the scope of the claims that follow.

What is claimed is:

1. A process for the preparation of a (1R,3R)- or a (1S,3S)-2,2-dihalo-3-(substituted phenyl)cyclopropanecarboxylic acid of Formula 1-2A or Formula 1-2B

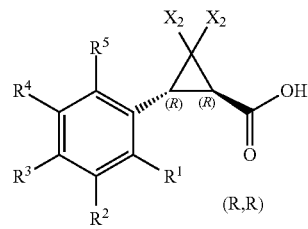

1-2A

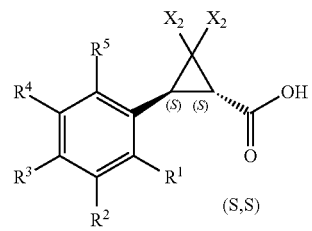

1-2B wherein:

(A) $R^1$ is selected from the group consisting of H, F, Cl, Br, I, CN, $NO_2$, $SF_5$, $(C_1-C_3)$alkyl, and $(C_1-C_3)$haloalkyl;

(B) $R^2$ is selected from the group consisting of H, F, Cl, Br, I, CN, $NO_2$, $SF_5$, $(C_1-C_3)$alkyl, and $(C_1-C_3)$haloalkyl;

(C) $R^3$ is selected from the group consisting of H, F, Cl, Br, I, CN, $NO_2$, $SF_5$, $(C_1-C_3)$alkyl, and $(C_1-C_3)$haloalkyl;

(D) $R^4$ is selected from the group consisting of H, F, Cl, Br, I, CN, $NO_2$, $SF_5$, $(C_1-C_3)$alkyl, and $(C_1-C_3)$haloalkyl;

(E) $R^5$ is selected from the group consisting of H, F, Cl, Br, I, CN, $NO_2$, $SF_5$, $(C_1-C_3)$alkyl, and $(C_1-C_3)$haloalkyl; and (G) $X^2$ is selected from the group consisting of F, Cl, Br, and I; comprising:

a) treating a racemic mixture of a trans-2,2-dihalo-3-(substituted phenyl)cyclopropane-carboxylic acid of Formula 1-1

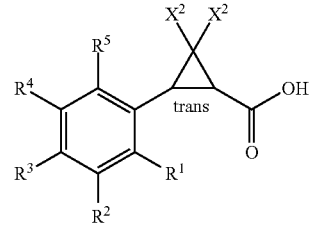

1-1 with an enantiomeric amine of Formula 2-1 or 2-2

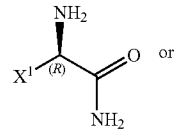

2-1

-continued

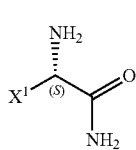
2-2 wherein:
X¹ is selected from the group consisting of $C_1$-$C_4$ alkyl and benzyl;
to form a mixture;
b) isolating a diastereomeric amine salt of Formula 3-1A or Formula 3-1B,

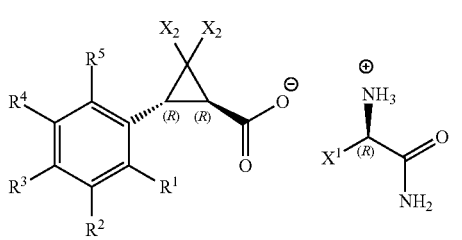
3-1A

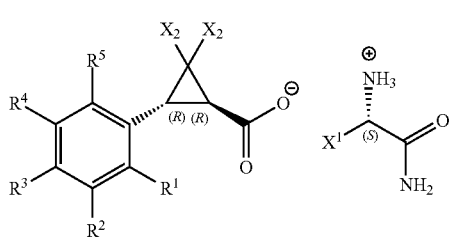
3-1B or of Formula 3-2A or Formula 3-2B,

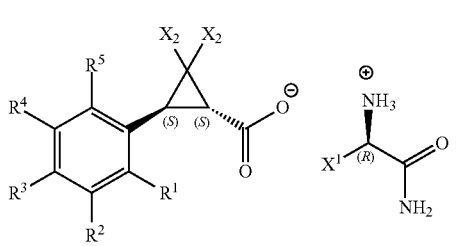
3-2A

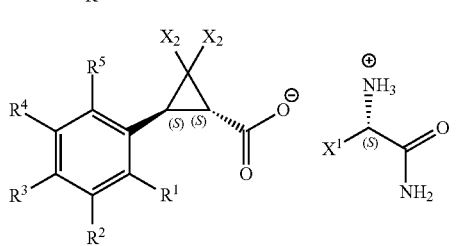
3-2B from the mixture; and
c) treating the isolated diastereomeric amine salt of Formula 3-1A or 3-1B, or of Formula 3-2A or 3-2B, with an acid to provide the (1R,3R)- or the (1S,3S)-2,2-dihalo-3-(substituted phenyl)cyclopropanecarboxylic acid of Formula 1-2A or Formula 1-2B.

2. The process of claim 1 wherein from about 0.4 to about 0.7 molar equivalents of the enantiomeric amine of Formula 2-1 or 2-2 is combined with the racemic mixture of the trans-2,2-dihalo-3-(substituted phenyl)cyclopropane-carboxylic acid of Formula 1-1.

3. The process of claim 1 wherein the isolating the diastereomeric amine salt of Formula 3-1A or Formula 3-1B, or of Formula 3-2A or Formula 3-2B comprises separating the diastereomeric amine salt from the crude reaction mixture by filtration or centrifugation.

4. The process of claim 1 wherein the acid may be selected from the group consisting of hydrochloric acid, hydrobromic acid, sulfuric acid, phosphoric acid, and nitric acid.

5. The process of claim 1 wherein $R^1$ and $R^5$ are H.

6. The process of claim 5 wherein $R^2$ is selected from the group consisting of H, F, and Cl, $R^3$ is F or Cl, and $R^4$ is selected from the group consisting of F, Cl and ($C_1$-$C_6$) haloalkyl.

7. The process of claim 1 wherein the enantiomeric amine of Formula 2-2 is (L)-leucinamide.

8. The process of claim 1 wherein the enantiomeric amine of Formula 2-1 is (D)-phenylalanine amide.

9. The process of claim 1 wherein the enantiomeric amine of Formula 2-2 is (L)-phenylalanine amide.

10. A process for the preparation of a (1R,3R)-2,2-dichloro-3-(3-trifluoromethyl-4-fluorophenyl)cyclopropanecarboxylic acid of Formula 4-1

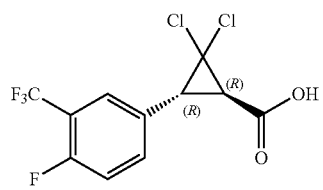
4-1 comprising:
a) treating a racemic mixture of trans-2,2-dichloro-3-(3-trifluoromethyl-4-fluorophenyl)cyclopropane-carboxylic acid of Formula 4-2

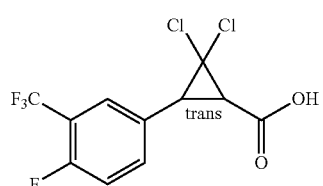
4-2 with an enantiomeric amine of Formula 2-2A

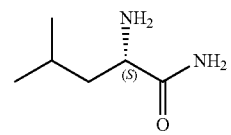
2-2A to form a mixture;
b) isolating a diastereomeric amine salt of Formula 4-3
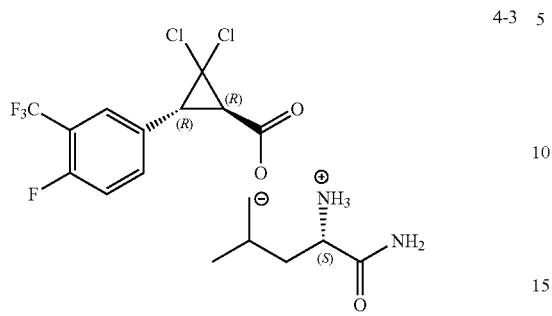
4-3
from the mixture; and
c) treating the isolated diastereomeric amine salt of Formula 4-3 with an acid to provide the (1R,3R)-2,2-dichloro-3-(3-trifluoromethyl-4-fluorophenyl)cyclopropanecarboxylic acid of Formula 4-1.
* * * * *